US00PP30039P2

(12) United States Plant Patent
Hansen

(10) Patent No.: US PP30,039 P2
(45) Date of Patent: Dec. 25, 2018

(54) ***SEDUM* PLANT NAMED 'LITTLE MISS SUNSHINE'**

(50) Latin Name: ***Sedum* hybrid**
Varietal Denomination: Little Miss Sunshine

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/731,916

(22) Filed: Aug. 22, 2017

(51) Int. Cl.
*A01H 5/02* (2018.01)

(52) U.S. Cl.
USPC ..... Plt./479
CPC ..... *A01H 5/02* (2013.01)

(58) Field of Classification Search
USPC ..... Plt./479
See application file for complete search history.

*Primary Examiner* — Anne Marie Grunberg

(57) ABSTRACT

The new and distinct cultivar of perennial *Sedum* plant named 'Little Miss Sunshine' is characterized by drought-tolerant, winter-hardy, tight, low, clumps, flower stems that remain upright in the center of the plant throughout the growing season, small, dark-green, glossy foliage and numerous bright yellow flowers clustered on small heads that completely covering the compact, low-mounded plant.

1 Drawing Sheet

Botanical designation: *Sedum* hybrid.
Cultivar denomination: 'Little Miss Sunshine'.

BACKGROUND OF THE INVENTION

The present invention relates to a new and distinct cultivar of *Sedum* or stonecrop plant, botanically known as *Sedum* and hereinafter referred to by the cultivar name 'Little Miss Sunshine'. There are over 300 recognized species of the genus *Sedum*.

The new plant is a selection of a planned breeding program conducted by the inventor at a wholesale perennial nursery in Zeeland, Mich., USA between an unnamed proprietary selection of *Sedum kamtschaticum* sp. *ellecombianum* (not patented) x a distinct unnamed proprietary seedling of *Sedum kamtschaticum* sp. *ellecombianum* (not patented) in the summer of 2012. The seeds were collected in the fall of 2012, and the individual plant originating from the single seedling selection was given the breeder code 12-67-3 in 2014 at the end of evaluation process at the same nursery.

The new *Sedum* plant was selected for its compact groundcover habit form together with the cheery, bright-yellow flower color and particularly the dark green foliage.

Asexual reproduction of *Sedum* 'Little Miss Sunshine' by vegetative cuttings at a wholesale perennial nursery in Zeeland, Mich., USA since the summer of 2014, has shown that the unique features of this new *Sedum* plant are stable and reproduced true to type in successive generations.

No plants of *Sedum* 'Little Miss Sunshine' have been sold in this country, or anywhere in the world, prior to the filing of this application, nor has any disclosure of the new plant been made prior to the filing of this application with the exception of that which was disclosed or sold within one year of the filing of this application and was either derived directly or indirectly from the inventor.

SUMMARY OF THE INVENTION

Plants of *Sedum* 'Little Miss Sunshine' have not been observed under all possible environmental conditions. The phenotype may vary somewhat with variations in environment such as temperature, available water, fertility and light intensity without, however, any variation in genotype.

The following traits have been repeatedly observed and are determined to be the unique characteristics of *Sedum* 'Little Miss Sunshine'. The following characteristics in combination distinguish 'Little Miss Sunshine' as a new and distinct *Sedum* plant unique from all other *Sedum* plants known to the inventor:

1. Short and compact plant habit.
2. Plants are drought tolerant and winter hardy to at least USDA zone 3.
3. Small, dark-green, glossy foliage produced on short stiff stems.
4. Numerous, bright yellow flowers in clusters nearly completely cover the plant in early summer.

In comparison to the female and male parents the new plant forms a denser and more compact clump, and the flowers of 'Little Miss Sunshine' are similar in their bright, cheery yellow color, but the clusters are smaller on the parent plant. The most unique difference is the dark green foliage.

Other similar plants include *Sedum* 'Lime Twister' U.S. Plant Pat. No. 26,895 and *Sedum* 'Lime Zinger' U.S. Plant Pat. No. 24,632. Both 'Lime Twister' and 'Lime Zinger' have similar habit, but the foliage is rounded and grayed green with flowers that are cream with purplish red tinting. The foliage of 'Lime Twister' is also variegated.

'Little Miss Sunshine' can also be compared with *Sedum* 'Pure Joy' U.S. Plant Pat. No. 24,194 that differs from the new plant by having blue-green foliage with light purplish pink flowers.

BRIEF DESCRIPTION OF THE PHOTOGRAPH

The photograph of the new plant demonstrates the unique traits and the overall appearance of *Sedum* 'Little Miss Sunshine'. The colors are as accurate as reasonably possible with color reproductions of this type. Variations in ambient light spectrum, source and direction may cause the appearance of minor variation in color. The plants used in the photographs were two-year old plants grown in an open, full-sun trial garden at a wholesale perennial nursery in Zeeland, Mich. with supplemental water and fertilizer when needed. No plant growth regulators have been used.

DETAILED BOTANICAL DESCRIPTION

Figure 1:
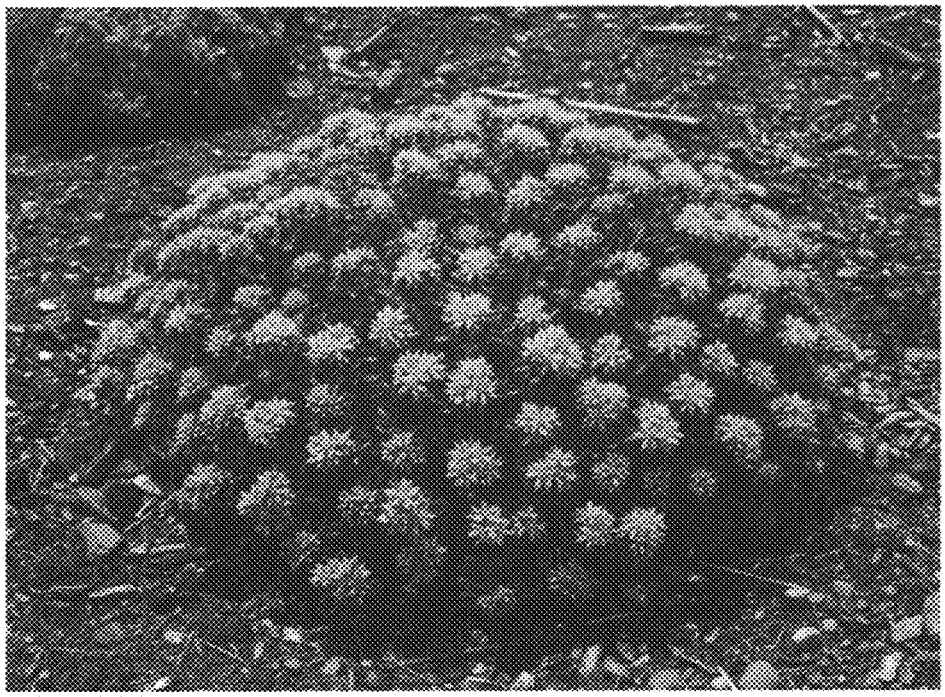
FIG. 1 shows the plant in full flower habit.
Figure 2:
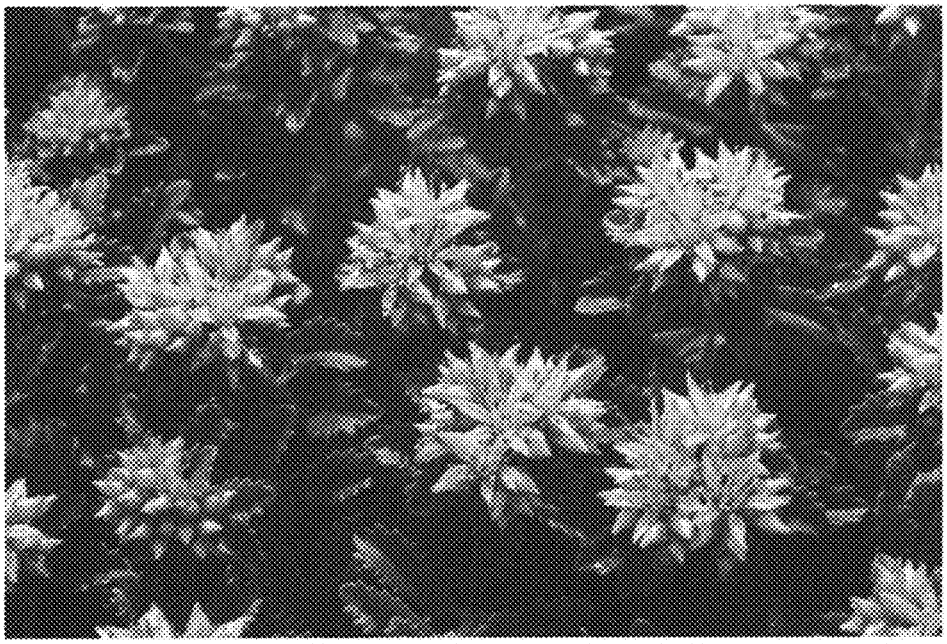
FIG. 2 shows a close-up of the flowers and buds.

The following is a detailed description of two year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Little Miss Sunshine';

Parentage: The female or seed parent is unreleased, proprietary seedling of *Sedum kamtschaticum* sp. *ellecombianum* (not patented) and the male or pollen parent is a distinct unreleased, proprietary seedling of *Sedum kamtschaticum* sp. *ellecombianum;*

Asexual propagation: Stem cuttings and division;

Time to initiate roots: About two weeks;

Time to finish a 3.7 liter flowering container: About three months in the summer from a rooted 2.5 cm plug;

Root description: Thick, fleshy; freely branching; creamy white to light tan in color.

Plant habit: Winter-hardy, succulent, herbaceous perennial; low mounded; multiple stiff stems, upright to outright, arising from a dense base; flower heads freely branching; dense and full, not developing open center later in the season;

Growth rate: Moderately vigorous;

Plant size: About 18.0 cm tall and 38.0 cm wide in full flower;

Main stems: Glabrous; about 40 per plant; diameter at base about 2.5 mm, about 10 cm long from base to initial flower cymes; maintaining foliage to base of stem; internodes average about 0.6 cm;

Main stem color: Blend between RHS 144A and RHS 138B;

Lateral branches: Glaucous; about 1.5 mm diameter for lowest level branching and about 10.0 cm long;

Lateral branch color: Nearest RHS 136D;

Foliage: Opposite, simple; ovate; smooth; glabrous abaxial and adaxial; nitid adaxial, and matte abaxial; base sessile to attenuate; apex rounded; margin crenate in distal one-half to one-third and entire in basal one-half to two thirds; thick, fleshy and succulent; to about 3.5 cm long and about 2.0 cm across near apex, average about 3.1 cm long, about 1.2 mm thick, about 1.8 cm across at widest portion just below apex, and base tapering to about 1.5 mm across; decreasing in size distally;

Foliage color: Developing leaves variable — adaxial surface between RHS 144A and RHS N144D in basal portion and nearest RHS 137A distally, abaxial surface between RHS 144A and RHS N144D in basal portion and distally nearest RHS 137B; fully developed leaves at flowering time — adaxial surface nearest RHS 137A, abaxial surface blend between RHS 137C and RHS 146B;

Venation: Pinnate; color same as surrounding leaf tissue on both surfaces;

Flower: Rotate; upright; perfect; actinomophic; in terminal compound cymes; freely flowering habit with up to 55 flower buds and flowers per terminal branched cyme, 130 per branched stem and 2,000 to 4,000 per plant, covering nearly the entire foliage;

Flower size: About 18.0 mm across and 8.0 mm long;

Flower facing: Upward to outwardly;

Flower fragrance: Not detected;

Flowering season: Beginning early summer and continuing for about four weeks in Zeeland, Mich.;

Longevity: Individual flower remain effective for about four to six days on the plant and as cut flowers; individual flowers persistent;

Flower buds about one day prior to opening: Broadly elliptic; apex acute; base rounded; about 10.0 mm long and 3.5 mm across;

Flower bud color: Exposed petals nearest RHS 1B with longitudinal stripes of between RHS 145A and RHS N144D;

Inflorescence: About 7.0 cm tall from first branch and 9.0 cm across; about 55 flowers per center cyme and 14 per cyme branch;

Petals: Typically six, lanceolate; acute apex, base fused, margin entire, glabrous; typically about 9.0 mm long and about 2.0 mm across;

Petal color: Adaxial nearest RHS 2A with abaxial margin 1A and abaxial longitudinal center nearest RHS 151B;

Sepals: Typically six, lanceolate; entire; glabrous and nitid abaxial and adaxial; subacute apex, truncate fused base; campanulate; about 5.0 mm long and about 1.5 mm wide at fused base;

Sepal color: Nearest RHS 137A both adaxial and abaxial surfaces;

Peduncles: Glabrous; terete; strong and stiff, yet flexible; freely branching; angle erect in center to nearly 60 degrees from perpendicular for branched portions; about 7.0 cm long and 1.5 mm diameter;

Peduncle color: Nearest RHS 138B;

Pedicels: Short to absent; terete; nitid; glabrous; strong and stiff, yet flexible; to about 3.5 mm long and 0.5 mm diameter;

Pedicel color: Nearest RHS 138A;

Androecium: Stamens: typically ten; to 7.0 mm long;

*Filaments*.—Thin; terete; upright; fused to petal base; about 6.0 mm long and about 0.5 mm diameter; color between RHS 1A and RHS 1B.

*Anthers*.—Ellipsoidal; basifixed; longitudinal; about 1.0 mm long and about 0.5 mm wide; color between RHS 14A and RHS 14B.

*Pollen*.—Abundant; color nearest RHS 14A.

Gynoecium: Typically five, rarely four or six; cylindrical, conic in distal one third;

*Style*.—About 2.0 mm long and 0.5 mm diameter at point of attachment to ovary; glabrous; color nearest RHS N144C.

*Stigma*.—Minute; color nearest N144C.

*Ovary*.—Nearly cylindrical, tapering at apex to style; about 5.5 mm long and 2.0 mm diameter; color nearest RHS N144C.

Seed and fruit: Have not yet been observed;

Disease and pest resistance: Plants of the new *Sedum* 'Little Miss Sunshine' grow best with good drainage, full sun and moderate to low fertility. 'Little Miss Sunshine' is cold hardy from USDA zones 3 to 9. 'Little Miss Sunshine' tolerates heavy rains and wind and does not tend to develop an open center later in the season as many other stonecrop cultivars do. *Sedum* 'Little Miss Sunshine' is not prone to rabbit damage. Other pest and disease resistance and tolerance outside that normal for stonecrop is not known.

It is claimed:

1. The new and distinct perennial *Sedum* plant named 'Little Miss Sunshine' as herein described and illustrated useful for landscaping as a specimen plant, en masse or as a cut flower.

* * * * *